United States Patent
Blaszczykiewicz et al.

(10) Patent No.: US 6,269,814 B1
(45) Date of Patent: Aug. 7, 2001

(54) SLEEP APNEA HEADGEAR

(75) Inventors: Thomas J. Blaszczykiewicz, Hamburg; David E. Holfoth, Lewiston, both of NY (US)

(73) Assignee: Accu-Med Technologies, Inc., Buffalo, NY (US)

( * ) Notice: Subject to any disclaimer, the term of this patent is extended or adjusted under 35 U.S.C. 154(b) by 0 days.

(21) Appl. No.: 09/594,067

(22) Filed: Jun. 14, 2000

Related U.S. Application Data

(60) Provisional application No. 60/139,973, filed on Jun. 18, 1999.

(51) Int. Cl.[7] .............. A61M 16/00; A62B 9/06
(52) U.S. Cl. .............. 128/207.17; 128/201.22; 128/201.29; 2/171.2
(58) Field of Search .............. 128/200.27, 200.28, 128/201.22, 201.24, 204.11, 207.11, 207.17, 207.18, 26, 846, 857; 2/173, 171.2, 209.13, DIG. 15, 251, 410, 425, 918, 909, 417, 195.2, 195.3

(56) References Cited

U.S. PATENT DOCUMENTS

| | | | |
|---|---|---|---|
| 4,703,879 | * 11/1987 | Kastendieck et al. | 224/121 |
| 4,766,610 | * 8/1988 | Mattes | 2/6 |
| 5,542,128 | * 8/1996 | Lomas | 2/173 |
| 5,564,128 | * 10/1996 | Richardson | 2/422 |

\* cited by examiner

*Primary Examiner*—Glenn K. Dawson
*Assistant Examiner*—Darwin P. Erczo
(74) *Attorney, Agent, or Firm*—Simpson, Simpson & Snyder, L.L.P.

(57) ABSTRACT

A sleep apnea headgear for positioning breathing apparatus on the head of a user includes a T-shaped rear portion and a T-shaped front portion each having latitudinal and longitudinal legs and a chinstrap made from a stretchable, breathable, laminated neoprene substitute having an inner surface of LYCRA® fabric and an outer surface of UBL loop material. The rear portion includes a hook-and-loop fastener at opposite lateral segments of its latitudinal leg for securing opposite ends of the chinstrap to the outer surface of the latitudinal leg, and a hook pad on the inner surface at each lateral end of the latitudinal leg. The front portion includes a slot opening at each lateral end of its latitudinal leg sized for receiving a corresponding lateral end of the latitudinal leg of the rear portion, whereby the hook pads may be attached directly to the outer loop surface of the latitudinal leg of the front portion. The front portion preferably includes its own hook pad on its inner surface at a distal end of the longitudinal leg for connecting to the outer surface loop material of the longitudinal leg of the rear portion. The assembled headgear is free of hook and/or loop pads openly facing the head or skin, and is also free of chemical adhesives.

3 Claims, 3 Drawing Sheets

SLEEP APNEA HEADGEAR

CROSS-REFERENCE TO RELATED APPLICATIONS

The present application claims the benefit of U.S. Provisional Application Ser. No. 60/139,973 filed Jun. 18, 1999.

BACKGROUND OF THE INVENTION

A. Field of the Invention

The present invention relates generally to the field of medical devices, and more particularly to an improved headgear for holding breathing apparatus in position adjacent a face of a person during sleep for treating sleep apnea.

B. Description of the Prior Art

Applicants are aware of a prior art headgear for sleep apnea treatment apparatus comprising a T-shaped rear portion, a T-shaped front portion releasably attached to the T-shaped rear portion to form a shell or cap for the head, and a chin strap releasably attached to the assembled shell. Two adjustable loops are fixed along an outer surface of a longitudinal leg of the T-shaped front portion for holding an oxygen feeder tube. The various components of the prior art headgear are made from a stretchable layered fabric having an inner layer of lycra, and an outer layer of nylon each adhered to a middle layer of neoprene, with hook-and-loop fastening elements being sewn at various locations for attachment purposes.

In this headgear of the prior art, a pair of opposite lateral segments of a latitudinal leg of the T-shaped rear portion include elongated loop pads sewn to an inner surface thereof, and a horizontal leg of the T-shaped front portion includes a single elongated hook pad sewn to an outer surface thereof for receiving the loop pads on each opposite lateral segment of the rear portion to form a closed loop about the head. Drawbacks of this design include the fact that part of the loop pads on the inner surface of the horizontal leg of the T-shaped rear portion are in contact with skin and can cause discomfort or irritation, and the adhesive used to bond to the neoprene causes an allergic reaction in a significant number of wearers.

SUMMARY OF THE INVENTION

Therefore, it is an object of the present invention to provide an improved headgear for supporting breathing apparatus on the head of a sleep apnea sufferer that is comfortable to wear, durable, easy to adjust, and free of chemical adhesive.

A preferred embodiment of the present invention comprises a T-shaped rear portion having latitudinal and longitudinal legs, a T-shaped front portion having latitudinal and longitudinal legs, and a chin strap all made from a stretchable, breathable, laminated neoprene substitute having an inner surface of lycra and an outer surface of UBL loop material. The rear portion includes hook-and-loop fastening means at opposite lateral segments of its latitudinal leg for securing opposite ends of the chin strap to the outer surface of the latitudinal leg, and a hook pad on the inner surface at each lateral end of the latitudinal leg leg. The front portion includes a slot opening at each lateral end of its latitudinal leg sized for receiving a corresponding lateral end of the latitudinal leg of the rear portion, whereby the hook pads may be attached directly to the outer loop surface of the latitudinal leg of the front portion. The front portion also includes its own hook pad on its inner surface at a distal end of the longitudinal leg for connecting to the outer surface loop material of the longitudinal leg of the rear portion. At least one adjustable loop is positioned along the longitudinal leg of the front portion to secure an oxygen feeder tube in place. The assembled headgear is free of hook and/or loop pads contacting the skin.

BRIEF DESCRIPTION OF THE DRAWINGS

The nature and mode of operation of the present invention will now be more fully described in the following detailed description of the preferred embodiment taken with the accompanying drawing figures, in which.

DETAILED DESCRIPTION OF THE PREFERRED EMBODIMENT

Figure 1:
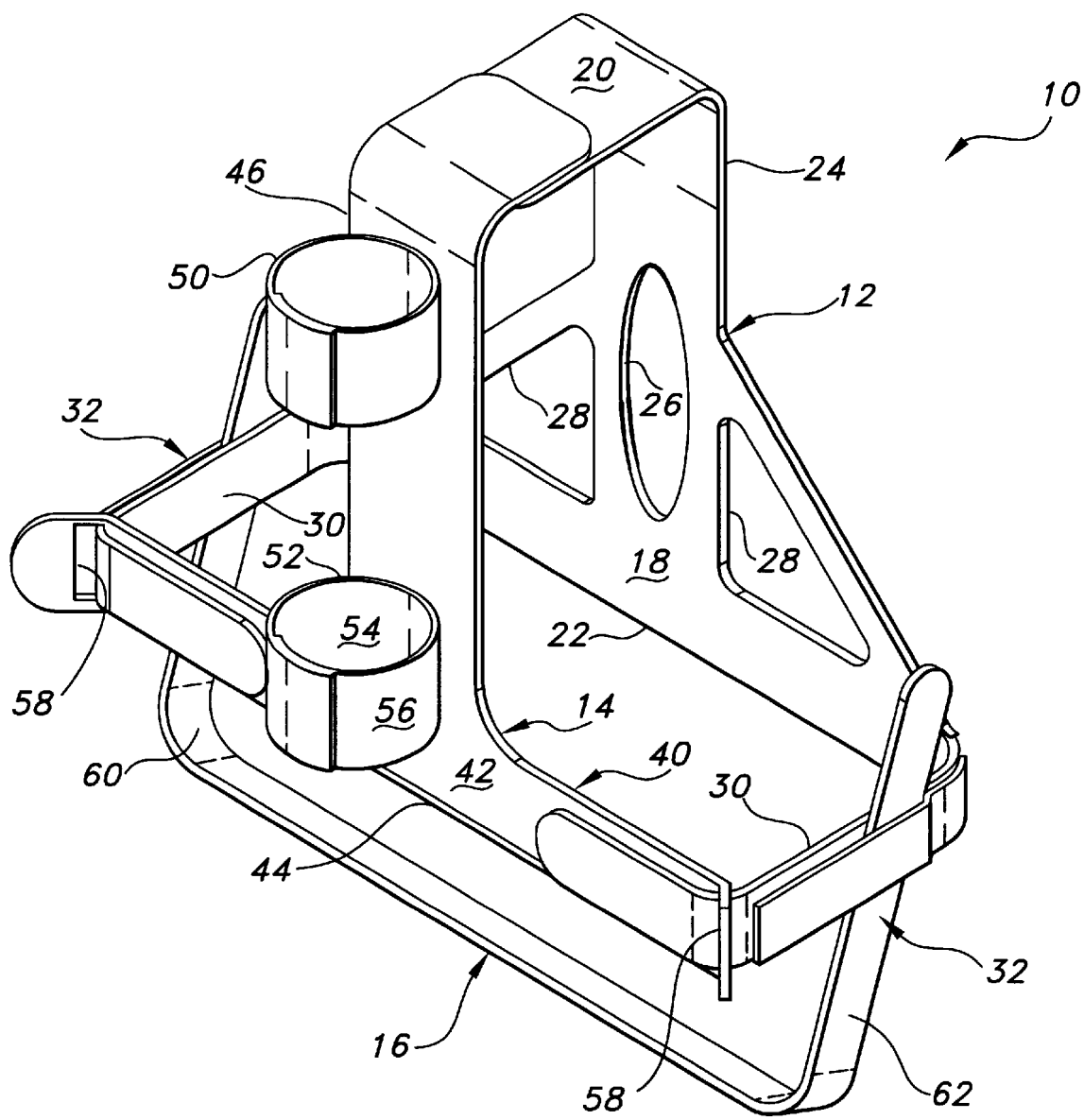
FIG. 1 is a perspective view of a sleep apnea headgear formed in accordance with a preferred embodiment of the present invention.

Referring initially to FIG. 1 of the drawings, a flexible sleep apnea headgear formed in accordance with a preferred embodiment of the present invention is shown and identified generally by the reference numeral 10. Headgear 10 is designed to be worn on the head of a sleep apnea sufferer for holding an oxygen tube feeding nasal pillows of a breathing apparatus, and is optimally constructed of BREATH-O-PRENE fabric available from Accu-Med Technologies Inc. of Buffalo, N.Y., assignee of the present application. Methods of manufacturing this fabric are described in commonly owned U.S. Provisional Patent Application Ser. No. 60/120,164 filed Feb. 16, 1999 and entitled "BREATHABLE NEOPRENE SUBSTITUTE", the specification of which is incorporated herein by reference. For the present invention, the fabric includes an inner layer of spandex fiber fabric such as LYCRA® fabric and an outer layer of UBL loop material each flame-laminated to a middle layer of compressed open-cell foam. Headgear 10 is illustrated as comprising a T-shaped rear portion 12, a T-shaped front portion 14 connected to T-shaped rear portion 12, and a chinstrap 16 also connected to rear portion 12. When assembled as described below, these components form an adjustable headgear.

Figure 2:
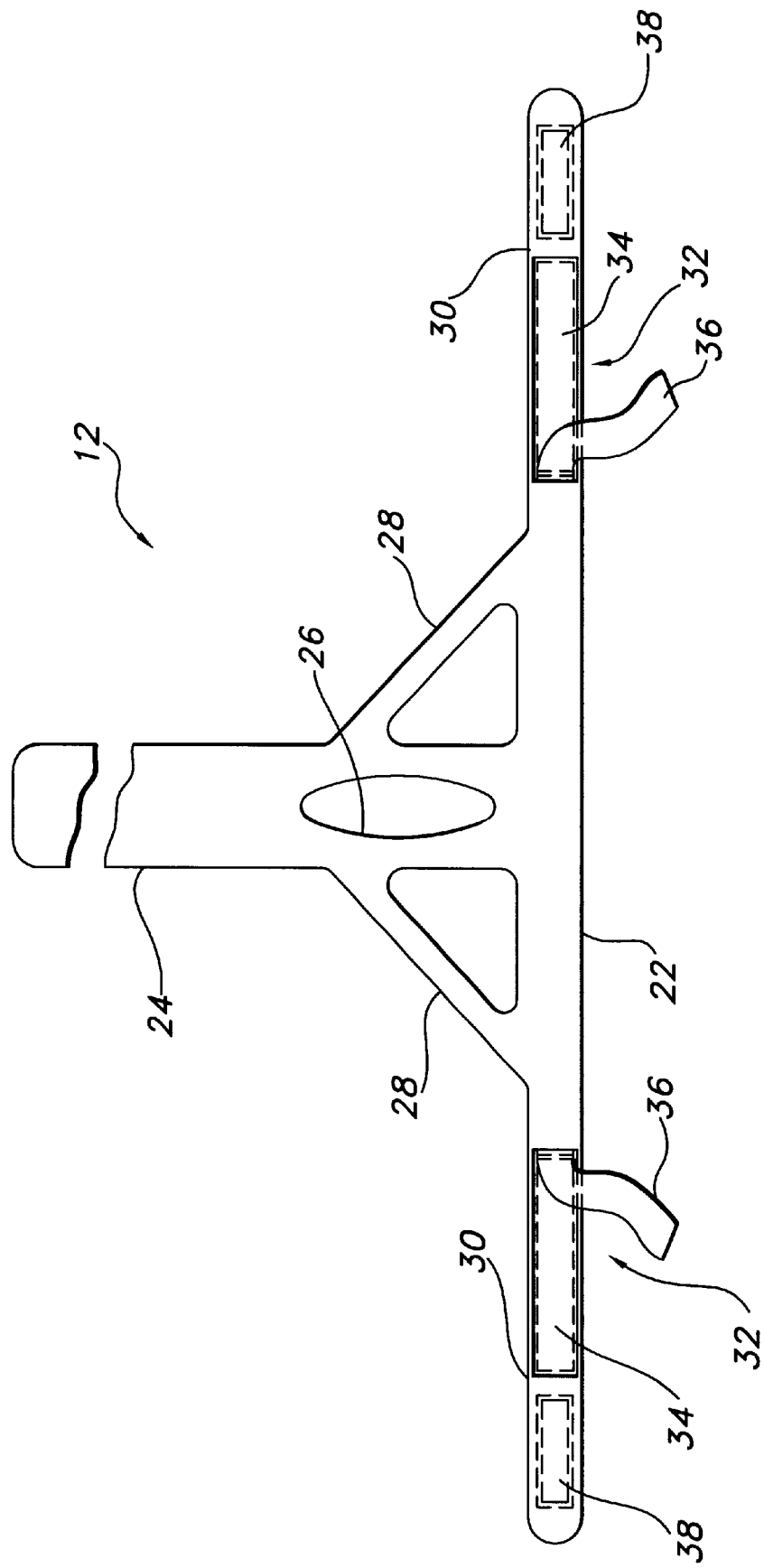
FIG. 2 is a plan view of a T-shaped rear portion of the sleep apnea headgear shown in FIG. 1.

T-shaped rear portion 12, shown in FIG. 2, includes an inner surface 18 of lycra material and an outer surface 20 of loop material. The configuration of rear portion 12 includes a latitudinal leg 22 and a longitudinal leg 24 extending from a mid-region of latitudinal leg 22. In order to redistribute tension at the junction between latitudinal leg 22 and longitudinal leg 24 and provide more comfortable air flow at the back of the head, longitudinal leg 24 is provided with an oval cut-out 26 and a pair of oblique connection members 28 on opposite sides thereof. Lateral segments 30 of latitudinal leg 22 are each provided with a hook-and-loop fastening means 32 having a hook pad 34 fixed to outer surface 20 and a flexible loop strap 36 facing hook pad 34 with one end fixed adjacent an end of hook pad 34 and an opposite end free for releasable attachment to the hook pad. A pair of hook pads 38 is provided on inner surface 18 of latitudinal leg 22, one at each lateral end.

Figure 3:
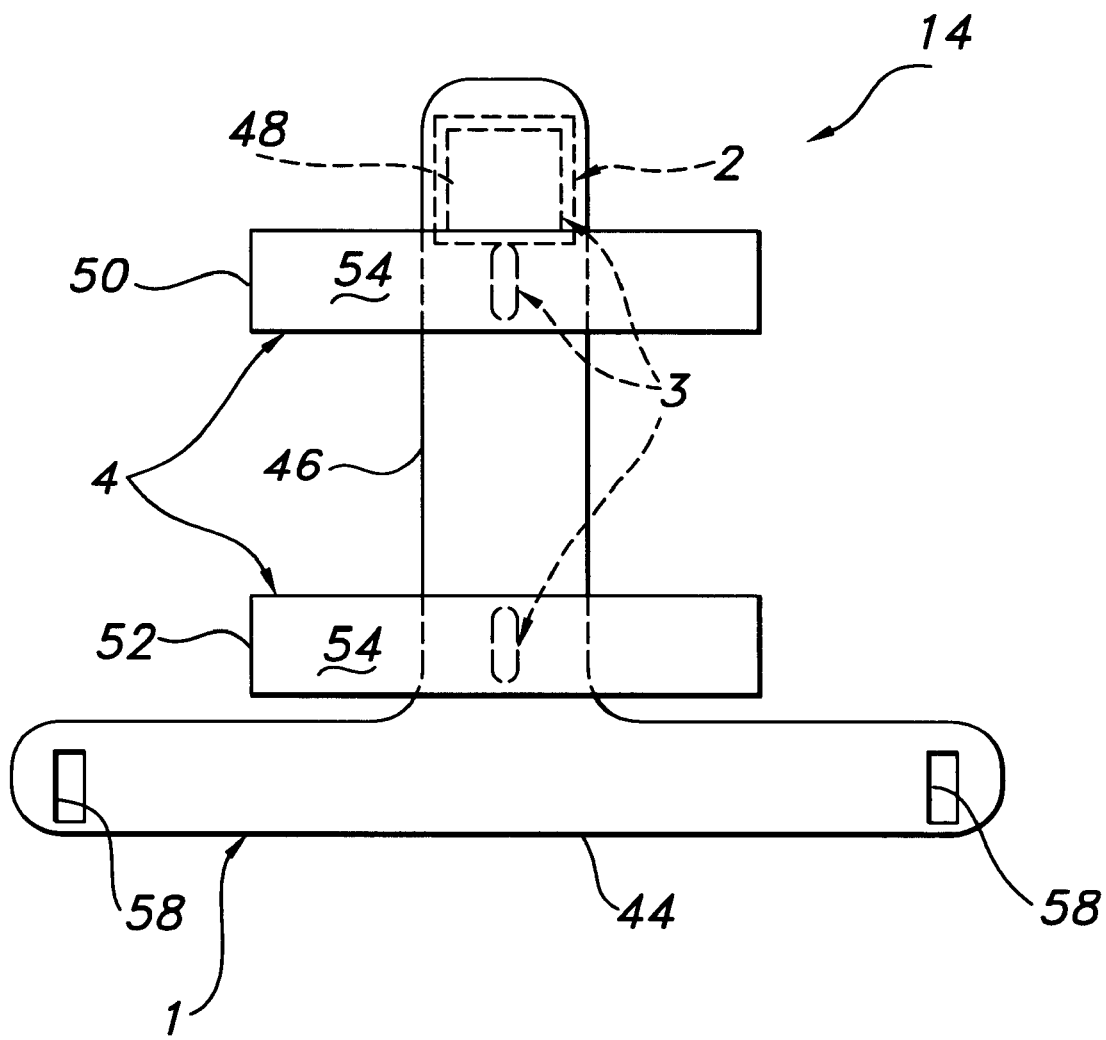
FIG. 3 is a plan view of a T-shaped front portion of the sleep apnea headgear shown in FIG. 1.

T-shaped front portion 14, shown in FIG. 3, includes an inner surface 40 of lycra and an outer surface 42 of loop material. Front portion 14 is configured to have a latitudinal leg 44 and a longitudinal leg 46 extending from a mid-region of latitudinal leg 44. A hook pad 48 is fixed to an inner surface of longitudinal leg 46 at a distal end of the longitudinal leg. Reference numerals 50 and 52 identify adjustable loops fixed to outer surface 42 near the distal end of longitudinal leg 46 and near a proximal end of longitudinal leg 46, respectively. Loops 50 and 52 are simply strips having an inner hook surface 54 and an outer loop surface 56 for closing the loop in a secure manner about the oxygen feeder tube. Latitudinal leg 44 includes a pair of slot openings 58, one at each lateral end thereof, sized to receive a corresponding hook pad 38 on latitudinal leg 22 of rear portion 12.

Chinstrap 16 is an elongated strip having an inner surface 60 of lycra and an outer surface 62 of loop material.

The manner of assembling rear portion 12, front portion 14, and chinstrap 16 to form headgear 10, and the manner of adjusting the assembled headgear, will now be described with reference again being made to FIG. 1. The distal end of longitudinal leg 46 of front portion 14 is attached to longitudinal leg 24 of rear portion 12 by connecting hook pad 48 directly to the loop material of outer surface 20 to form a meridian over the top of the head. Each lateral end of latitudinal leg 22 of rear portion 12 is fed through a respective slot opening 58 in latitudinal leg 44 of front portion 14 from inner surface 40 to outer surface 42, and hook pads 38 are connected directly to the loop material of outer surface 42. To secure chinstrap 16 to the assembly, opposite ends of the chinstrap are captured by corresponding fastening means 32 on rear portion 12. As will be understood, various size adjustments are possible by changing the location at which hook pad 48 connects to longitudinal leg 24, changing the locations at which hook pads 38 connect to latitudinal leg 44, and changing the locations at which chinstrap 16 is captured by fastening means 32.

In its assembled state, the inner surfaces 18, 40 and 60 of the respective components 12, 14 and 16 coming into contact with the head are free of hook and/or loop elements which may cause discomfort or irritation, and are also free of chemical adhesive which may cause an allergic reaction.

What is claimed is:

1. A headgear for securing a breathing apparatus in position near a face of a person for treating sleep apnea, said headgear comprising:

a T-shaped front portion of flexible fabric, said front portion including:

an inner surface, an outer surface of loop material opposite said inner surface, a latitudinal leg having a pair of slot openings located one at each opposite lateral end of said latitudinal leg, and a longitudinal leg extending from a location on said latitudinal leg between said pair of slot openings and having a hook pad at a distal end thereof on said inner surface;

a T-shaped rear portion of flexible fabric, said rear portion including:

an inner surface of said rear portion, an outer surface of loop material opposite said inner surface, a latitudinal leg having a pair of hook pads located one at each opposite lateral end of said latitudinal leg of said rear portion on said inner surface, of said rear portion and a longitudinal leg extending from a location on said latitudinal leg of said rear portion between said pair of hook pads;

said rear portion being releasably attached to said front portion by respective insertion of said pair of hook pads through said pair of slot openings and attachment of said pair of hook pads to said outer surface of said front portion and attachment of said hook pad at said distal end of said longitudinal leg of said front portion to said outer surface of said rear portion; and a chinstrap having opposite ends releasably attached to said outer surface of said rear portion.

2. The headgear according to claim 1, wherein said outer surface of said rear portion includes hook-and-loop fastening means at opposite lateral segments of said latitudinal leg of said rear portion for releasably attaching said opposite ends of said chinstrap in an adjustable manner.

3. The headgear according to claim 2, wherein said chinstrap includes an inner surface and an outer surface of loop material opposite said inner surface, of said chinstrap and said hook-and-loop fastening means captures said loop material on said outer surface of said chin strap.

\* \* \* \* \*